United States Patent
Samaranayake

(10) Patent No.: US 10,676,634 B2
(45) Date of Patent: Jun. 9, 2020

(54) MODIFIED LATENT CROSSLINKER IN POLYMERIC SYSTEMS

(71) Applicant: THE SHERWIN-WILLIAMS COMPANY, Cleveland, OH (US)

(72) Inventor: Gamini S Samaranayake, Cleveland, OH (US)

(73) Assignee: SWIMC LLC, Cleveland, OH (US)

(*) Notice: Subject to any disclaimer, the term of this patent is extended or adjusted under 35 U.S.C. 154(b) by 82 days.

(21) Appl. No.: 16/121,998

(22) Filed: Sep. 5, 2018

(65) Prior Publication Data
US 2020/0071559 A1    Mar. 5, 2020

(51) Int. Cl.
| | | |
|---|---|---|
| *C09D 133/26* | (2006.01) | |
| *C09D 7/63* | (2018.01) | |
| *C08J 3/24* | (2006.01) | |
| *C08K 3/22* | (2006.01) | |
| *C08K 5/25* | (2006.01) | |

(52) U.S. Cl.
CPC ............ *C09D 133/26* (2013.01); *C08J 3/24* (2013.01); *C08K 3/22* (2013.01); *C08K 5/25* (2013.01); *C09D 7/63* (2018.01); *C08J 2333/10* (2013.01); *C08J 2333/26* (2013.01); *C08K 2003/2241* (2013.01)

(58) Field of Classification Search
CPC .......... C09D 133/26; C09D 7/63; C08K 3/22; C08K 5/25; C08J 3/24; C08J 2333/26; C08J 2333/10
USPC ........................................................ 524/555
See application file for complete search history.

(56) References Cited

U.S. PATENT DOCUMENTS

| | | | |
|---|---|---|---|
| 4,250,070 A | 2/1981 | Ley et al. | |
| 9,139,699 B2 * | 9/2015 | Cook | C08G 77/08 |
| 9,469,799 B2 * | 10/2016 | Cook | C08G 77/08 |
| 9,809,697 B2 * | 11/2017 | Furo | C07C 243/28 |
| 2014/0100347 A1 * | 4/2014 | Cook | C08K 3/01 |
| | | | 528/15 |
| 2015/0337190 A1 * | 11/2015 | Cook | C09J 183/06 |
| | | | 528/15 |
| 2016/0237245 A1 * | 8/2016 | Furo | C07C 243/28 |

FOREIGN PATENT DOCUMENTS

| | | |
|---|---|---|
| EP | 3056535 | 8/2016 |
| JP | S5233948 | 3/1977 |
| WO | 2013138566 | 9/2013 |

OTHER PUBLICATIONS

X. Zhang et al., "The Diacetone Acrylamide Crosslinking Reaction and Its Control of Core-Shell Polyacrylate Latices at Ambient Temperature," Journal of Applied Polymer Science, (2012) vol. 123, pp. 1822-1832.

International Search Report and Written Opinion for international application no. PCT/US2018/049633, dated Jan. 3, 2020 (20 pages).

* cited by examiner

*Primary Examiner* — Michael Bernshteyn

(57) ABSTRACT

A self-crosslinking compound and coating compositions including the same as well as compositions capable of forming a ketone or carbonyl-hydrazide crosslink at ambient temperatures that utilizes a modified latent cross linker capable of forming a polymer networked in an applied coating.

32 Claims, 1 Drawing Sheet

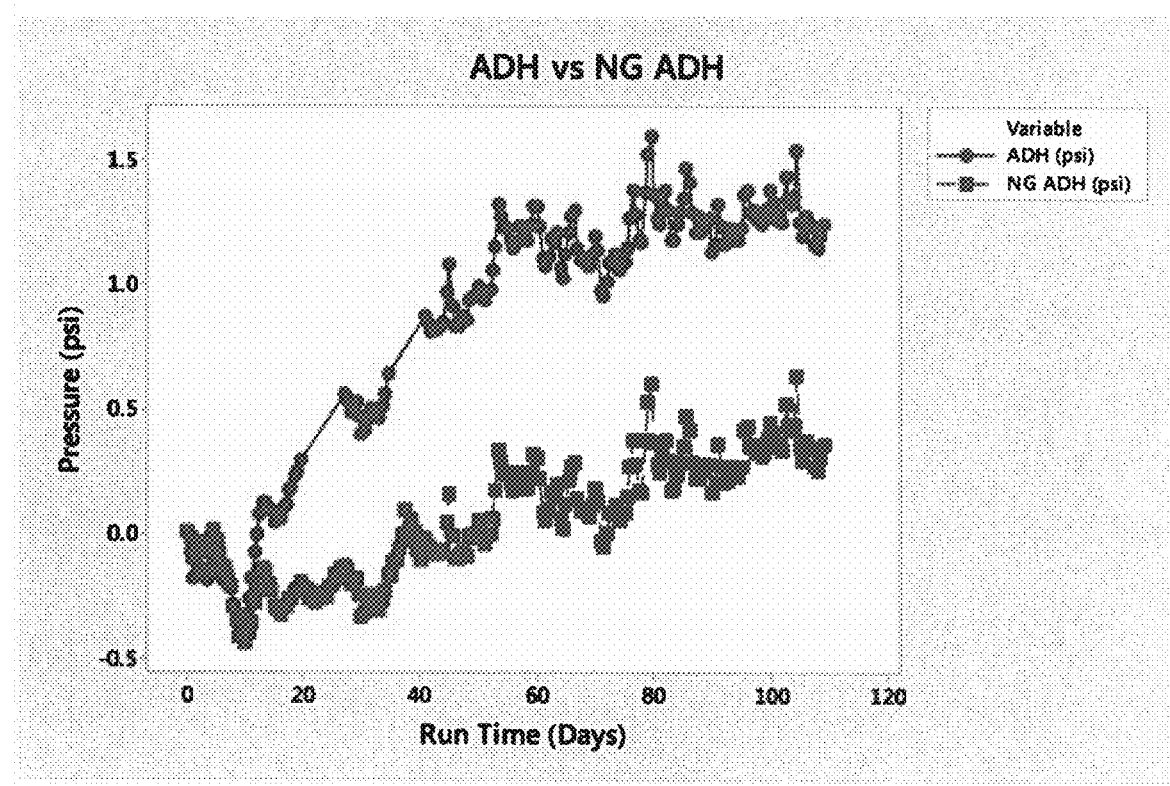

MODIFIED LATENT CROSSLINKER IN POLYMERIC SYSTEMS

FIELD

This application generally relates to self-crosslinking polymeric systems and compositions thereof and, more particularly, self-crosslinking polymer compositions having reduced levels of off-gassing.

BACKGROUND

Ambient temperature, self-crosslinking coating compositions often utilize a carbonyl- or ketone-hydrazide cross-linking reaction to achieve characteristics similar to conventional two-component crosslinking systems. After applying the coating to a substrate, the solvents and the buffering components evaporate to increase the acidity of the system, which initiates the cross-linking reaction between a carbonyl or ketone group often present on a polymer and a hydrazide group often present on a separate cross-linking agent to form a cross-linked coating or film.

In some cases, however, there is a shortcoming when using prior hydrazide cross-linking technology because high levels of outgassing can occur before the cross-linking reaction is initiated. This outgassing is detrimental not only to the container used to the hold the compositions, but also negatively affects the properties of the resultant coating. In some instances, the outgassing can be sufficiently excessive so that the lid of a conventional paint can or container can pop off or plastic containers develop unsightly bulges. Neither of which are acceptable to consumers. Even if the outgassing can be contained within a sturdier container or potentially vented out of the containers, the composition remaining after significant outgassing tends to have inferior performance as evidenced by lack of durability when applied as a coating.

SUMMARY

In one approach, a modified dihydrazide cross-linking compound is provided having the formula $H_2NN(R_1)C(O)R_2C(O)N(R_3)NH_2$ wherein $R_1$ and $R_3$ are independently selected from a C1 to C3 alkyl hydrocarbon or an alkyl residue bearing functional groups and $R_2$ is selected from a C1 to C12 alkyl hydrocarbon.

In other approaches, the modified Dihydrazide crosslinking compound of the previous paragraph may be combined with one or more further features either individually or in any combination. These further features include wherein the functional groups include carboxylic acid, hydroxyl, sulfate, sulfonate, phosphate, alkyl ether, thiol, thiol ether, amido groups and combinations thereof.

In another approach or embodiment, a coating composition to reduce nitrogen generation upon shelf storage is provided. In one aspect, the coating composition includes a polymer with monomer units including a ketone or carbonyl thereon, and a cross-linking compound of the formula $H_2NN(R_1)C(O)R_2C(O)N(R_3)NH_2$ wherein $R_1$ and $R_3$ are independently selected from a C1 to C3 alkyl hydrocarbon or an alkyl residue bearing functional groups and $R_2$ is selected from a C1 to C12 alkyl hydrocarbon.

In other approaches, the coating composition of the previous paragraph may be combined with one or more optional features, which may be selected from the following individually or in any combination: wherein the functional groups include carboxylic acid, hydroxyl, sulfate, sulfonate, phosphate, alkyl ether, thiol, thiol ether, amido groups and combinations thereof; and/or further comprising inorganic particles, but less than about 35 percent of the inorganic particles and one or more multivalent cation(s) selected from copper, iron, manganese, tin, cobalt, chromium, vanadium, and mixtures; and/or wherein the polymer includes one or more of acrylic, acrylate, acetate, styrene, alkyd, or combinations thereof monomer units; and/or wherein the polymer is selected from the group of poly-acrylate, poly-vinyl acetate-acrylate, polystyrene acrylate, or alkyd-acrylic hybrid polymers and wherein monomer units include a vinyl group polymerized into a polymer backbone and wherein at least one monomer unit has a side group extending from the vinyl group and having the ketone or carbonyl therein; and/or wherein the polymer is an acrylic latex and the monomer units with the ketone or carbonyl thereon include a vinyl group polymerized into a polymer backbone and further includes a side group having an amido nitrogen and the ketone or carbonyl thereon; and/or wherein the coating composition includes about 45 to about 60 weight percent of the polymer and about 0.5 to about 5 weight percent (in other approaches, about 1.5 to about 3 weight percent) of the cross-linking compound; and/or wherein the coating composition includes about 1 to about 500 ppm of the one or more multivalent cations(s); and/or wherein the cross-linking compound includes an alkyl modified hexanedihydrazide wherein the $R_1$ and $R_3$ group are methyl; and/or wherein the monomer units with the ketone or carbonyl thereon include diacetone acrylamide, diacetone methacrylamide, acetylacetoxy ethyl methacrylate, and combinations thereof; and/or wherein the inorganic particles include titanium dioxide and wherein the coating composition includes about 1 to about 35 percent of the titanium dioxide.

In yet a further approach or embodiment, a coating composition to reduce nitrogen generation is provided herein. In some aspects, the coating composition includes a polymer with monomer units including a ketone or carbonyl thereon and a cross-linking compound of the formula $H_2NN(R_1)C(O)R_2C(O)N(R_3)NH_2$ wherein $R_1$ and $R_3$ are independently selected from a C1 to C3 alkyl hydrocarbon or an alkyl residue bearing functional groups and $R_2$ is selected from a C2 to C12 alkyl hydrocarbon. The coating composition includes inorganic particles, but less than about 35 percent of the inorganic particles; and one or more multivalent cation(s) selected from copper, iron, manganese, tin, cobalt, chromium, vanadium, and mixtures thereof.

In other approaches, the coating composition of the previous paragraph may be combined with one or more optional features, which may be selected from the following individually or in any combination: wherein the functional groups include carboxylic acid, hydroxyl, sulfate, sulfonate, phosphate, alkyl ether, thiol, thiol ether, amido groups and combinations thereof; and/or wherein the monomer units with the ketone or carbonyl include an amido side group; and/or wherein the polymer is an acrylic latex and the monomer units include a vinyl group polymerized into a polymer backbone and the monomer units having the ketone or carbonyl thereon include an amido side group with the ketone or carbonyl at a terminal end of the side group; and/or wherein the coating composition includes about 45 to about 60 weight percent of the polymer and about 0.5 to about 5 weight percent (in other approaches, about 1.5 to about 3 weight percent) of the cross-linking compound; and/or wherein the coating composition includes about 1 to about 500 ppm of the one or more multivalent cations(s); and/or wherein the cross-linking compound includes an alkyl modified hexanedihydrazide wherein the $R_1$ and $R_3$ groups are methyl; and/or wherein the monomer units include diacetone acrylamide, diacetone methacrylamide, acetylacetoxy ethyl methacrylate, and combinations thereof; and/or wherein the inorganic particles includes titanium dioxide and wherein the coating composition includes about 1 to about 35 percent of the titanium dioxide.

In yet a further approach or embodiment. a cross-linked polymer is provided. In some aspects, the cross-linked polymer includes a reaction product of (1) a polymer including acrylic, acrylate, acetate, styrene, alkyd, urethane, or combinations thereof monomer units and monomer units with a pendant ketone or carbonyl thereon and (2) a cross-linking compound of the formula $H_2NN(R_1)COR_2CON(R_3)NH_2$ wherein $R_1$ and $R_3$ are independently selected from a C1 to C3 alkyl hydrocarbon or an alkyl residue bearing functional groups thereof and $R_2$ is selected from a C2 to C12 alkyl hydrocarbon. The reaction of (1) and (2) occurs at about 20° C. to about 30° C. in the presence of one or more multivalent cation(s) selected from copper, iron, manganese, tin, cobalt, chromium, vanadium, and mixtures thereof.

In other approaches, the cross-linked polymer of the previous paragraph may be combined with one or more optional features, which may be selected from the following individually or in any combination: wherein the functional group are selected from one of carboxylic, hydroxyl, sulfate, sulfonate, phosphate, alkyl ether, thiol, thiol ether, amido groups or combinations thereof; and/or wherein prior to the formation of the reaction product of (1) and (2), a composition of an unreacted polymer (1) and an unreacted cross-linking compound (2) is free of nitrogen gas after 120 days of storage; and/or wherein a dried coating composition including the cross-linked polymer exhibits at least 200 scrubs; and/or wherein the polymer is an acrylic latex and includes a vinyl group polymerized into a polymer backbone and having an amido side group with the ketone or carbonyl therein; and/or further comprising about 45 to about 60 percent of the polymer or copolymer and about 0.5 to about 5 weight percent (in other approaches, about 1.5 to about 3 weight percent) of the cross-linking compound; and/or wherein the reaction occurs in the presence of about 1 to about 500 ppm of the one or more multivalent cations(s); and/or wherein the cross-linking compound includes an alkyl modified hexanedihydrazide wherein the $R_1$ and $R_3$ groups are methyl; and/or wherein the monomer units include diacetone acrylamide, diacetone methacrylamide, acetylacetoxy ethyl methacrylate, and combinations thereof; and/or wherein the reaction product is included in a paint composition including about 1 to about 35 percent titanium dioxide.

BRIEF DESCRIPTION OF DRAWINGS

FIG. 1 is a graph of nitrogen outgassing by cross-linker compound type.

DETAILED DESCRIPTION

A self-crosslinking coating composition including components capable of forming a ketone or carbonyl-hydrazide crosslink at ambient temperatures is provided herein that utilizes a modified latent cross linker capable of forming a polymer networked in an applied coating. Previously, malonic dihydrazide, adipic dihydrazide, hexanedioic acid dihydrazide, iso'phathalic dihydrazide, sebacic dihydrazides, and the like, were common latent cross-linkers used in the ketone or carbonyl-hydrazide self-crosslinking polymer systems. However, as mentioned above, there is a shortcoming with these prior cross-linkers in some circumstances that results in outgassing prior to the application of and the cross-linking of the composition. Discovered herein are modified latent cross-linkers, such as modified dihydrazide compounds, that arrest or reduce the outgassing found in some ketone- or carbonyl-hydrazide cross-linking systems.

Without wishing to be limited by theory, it is believed that the prior dihydrazide cross-linking agents can decompose in certain compositions and release nitrogen gas. Under some circumstances, this outgassing can be sufficiently excessive such that press-fit tops of conventional containers and paint cans can pop off under the pressure generated by this outgassing. In other circumstances, this outgassing reaction can generate unsightly swelling or bulging of plastic containers due to the build-up of nitrogen gas in the container.

Again not wishing to be limited by theory, it is believed that the prior unreacted dihydrazide can function as a reducing agent in the coating composition and generate nitrogen in an unintended redox reaction with an oxidant present in the composition. This reaction may be the result of small amounts of undesired contaminates or innocuous impurities in the composition. For instance, it is not uncommon for some coating compositions to include small amounts of multi-valent cations, such as copper, iron, manganese, tin, cobalt, chromium and/or vanadium metals. Small amounts of these cations may be introduced into the composition as innocuous impurities often present in various raw materials and/or obtained through the various processing equipment used to manufacture the composition. When present, it is believed that the prior dihydrazide component in the composition can reduce these innocuous multivalent cations in an easily reversible redox reaction in which nitrogen gas is generated from one or both of the hydrazide moieties on the cross-linking agent. For instance, during this interaction, nitrogen is generated by the redox reaction with the depletion of oxygen in the headspace of the container. This reaction results in the decomposition of the conventional dihydrazide cross-linking agent. Such undesired reaction generally renders the dihydrazide cross-linker ineffective for cross-linking due to the loss of one or both hydrazide groups, which can be observed by a decrease in scrub performance in an applied coating.

In one exemplary prior polymer system, it is believed that a copper/iron redox pair that may be present in the coating composition as innocuous impurities results in the redox reaction to generate nitrogen as shown by the exemplary process below when using a prior adipic dihydrazide as the latent cross-linking agent:

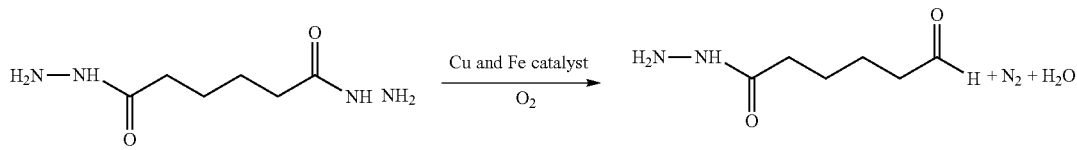

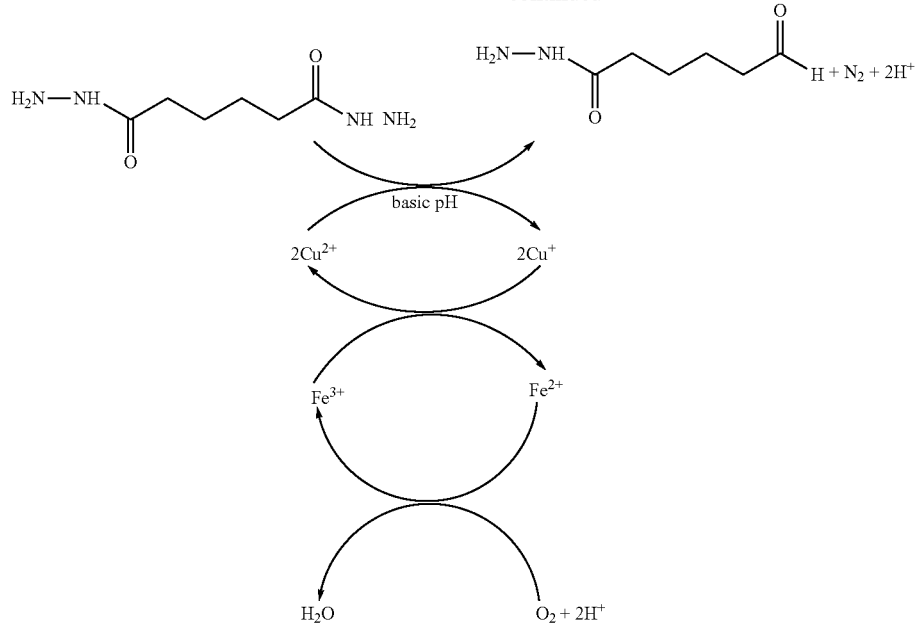

With the loss of a hydrazide moiety, the conventional latent cross-linking agent can no longer function as intended to cross-link with the ketone or carbonyl groups on a polymer in the composition. This decomposition of the conventional cross-linking agent results in a decrease in the durability of the applied coating and can be observed in a drop in scrub performance.

In systems without the prior dihydrazide cross-linking agent, the metal cation impurities are normally innocuous. In systems with the prior dihydrazide cross-linker, the presence of these impurities can affect cross-linking performance and outgassing as noted above. While the direct source of these cations is unknown, it is believed they may be introduced via various raw materials and/or derived from reactor vessels or mixing tanks used in the manufacture of the coating compositions. For example, copper, iron, or manganese may be introduced through raw materials (such as biocides, extenders, colorants, and/or extenders to suggest a few) or even through mixing or reactor vessels.

In some approaches, the compositions herein may include about 1 to about 500 ppm total of multi-valent metal cations (other than titanium), which may include about 5 to about 115 ppm of iron, about 0.01 to about 18 ppm of cobalt, about 0.001 to about 0.003 ppm of manganese, about 0.002 to about 5 ppm of copper, and about 0.001 to about 5 ppm of vanadium. In some approaches, Tables 1 and 2 below show the levels of various metals in samples of coatings and paints.

TABLE 1

Total levels of metals in dried neat paint

| Sample | Fe | Co | Mn | Ti | Cu | V |
|---|---|---|---|---|---|---|
| 1 | 33.6 | DL | DL | 38.3 | DL | DL |
| 2 | 11.4 | DL | DL | DL | DL | DL |
| 3 | 16.8 | 17.8 | DL | (12.3) | DL | 4.6 |
| 4 | 6.8 | DL | DL | (2.9) | DL | 0.6 |
| 5 | 14.1 | DL | DL | DL | DL | DL |
| 6 | 8.0 | 3.8 | DL | (2.7) | DL | 0.7 |
| 7 | 31.0 | DL | DL | 38.3 | DL | DL |
| 8 | 17.3 | 18.6 | DL | (13.0) | DL | 4.9 |

TABLE 2

Free element levels in a neat paint composition

| Sample | Fe | Co | Mn | V | Cu | Total | Ti |
|---|---|---|---|---|---|---|---|
| 1 | 31.9 | 2.2 | DL | DL | DL | 34.1 | DL |
| 2 | 8.5 | 2.3 | DL | DL | DL | 10.8 | DL |
| 3 | 30.1 | DL | DL | DL | DL | 30.1 | 336 |
| 4 | 8.8 | DL | DL | DL | DL | 8.8 | 1060 |
| 5 | 9.3 | DL | DL | DL | DL | 9.3 | DL |
| 6 | DL | DL | DL | DL | 1.6 | 1.6 | DL |
| 7 | 87.3 | DL | DL | DL | DL | 87.3 | DL |
| 8 | 113 | 2.8 | DL | DL | 1.5 | 117 | 824 |

In Table 1, total element levels for each sample in the dried whole paint is reported in ppm. Numbers in parenthesis are in weight percent units instead of ppm due to high concentration. Any cell marked "DL" indicated the element was below detection limit in that sample. For these total element levels of Table 1, each sample paint was dried, about 0.25 grams was digested into about 10 ml of nitric acid plus about 2 ml of hydrofluoric acid, and then diluted to about 100 ml. Analysis was completed through inductively coupled plasma spectroscopy (ICP). The detection limits in the final solution as run on the instrument were about 0.003 ppm for manganese, about 0.006 ppm for cobalt, about 0.3 ppm for titanium, about 0.002 ppm for copper, about 0.001 ppm for vanadium, and about 0.01 ppm for iron.

In Table 2, the free element levels in supernatant for each liquid sample is reported in ppm relative to whole paint. Numbers in parenthesis are in weight percent units instead of ppm due to high concentration. Any cell marked "DL"

indicated the element was below detection limit in that sample. The Total column of Table 2 represents the sum of the iron, copper, cobalt, manganese, and vanadium amounts and does not include the titanium in each paint. For the free element levels in Table 2, each paint was sampled using about 0.5 grams of wet paint, diluted into about 10 grams of 18 Mohm water and centrifuged at about 12,000 RPM for about 5 minutes. Then, about 5 mL of the supernatant was diluted to about 50 ml. A final filtering for solids was done using Whatmann 541 filters. The sample was analyzed using the same procedures as those discussed above relative to Table 1.

Again without wishing to be limited by theory, the outgassing reaction tends to be hindered in any composition including high levels of titanium, which is a common pigment in architectural paints and coating compositions. While not completely understood, paints and coating compositions with high levels of titanium dioxide, such as composition with greater than 35 percent, tend not to use higher levels of mineral extenders, such as clay and the like, which often bring heavy metals to the composition, which as noted above are suspected as leading to the decomposition of the prior hydrazides. Thus, the compositions herein that typically benefit from the new modified latent cross-linker described herein are self-crosslinking latex compositions utilizing a dihydrazide crosslinker to promote a keto/carbonyl-hydrazide crosslink and commonly called deep or ultra deep formulations with the levels of innocuous impurities noted above and with low levels of titanium dioxide such as 35 percent or less titanium dioxide or those with no titanium dioxide. These compositions that benefit from the new cross-linking composition herein are generally those with gloss values of about 5 to 50 and/or a PVC of about 10 to about 55.

Modified Latent Cross-Linker

The present application addresses these problems by utilizing a modified latent cross linking compound having at least two functional hydrazine moieties, such as an alkyl modified dihydrazide compound. As discussed above, the modified latent cross-linking compounds are used in combination with polymer systems including a pendant ketone or carbonyl side chain thereon. The combination of the modified latent cross linking compound and the polymer systems with the pendant ketone or carbonyl side chains thereon are self-crosslinkable at ambient conditions (such as about 25 to about 30° C.) and such components are capable of forming a bond or covalent link in the absence of any other cross-linking agents or materials. In some approaches, the self-cross-linkable composition forms bonds between the hydrazide functional groups on the modified latent cross-linking compound and the ketone or carbonyl groups on the polymer.

In some approaches, the modified latent cross-linker is an alkyl modified form of dicarboxylic acid bis-hydrazides, such as but not limited to, alkyl modified forms of malonic acid dihydrazide, oxalyl acid dihydrazide, iso-phthalic dihydrazide, succinic acid dihydrazide, adipic acid dihydrazide, or sebacic acid dihydrazide to suggest but a few examples. In other approaches, the alkyl-modified dihydrazide is exemplified by a compound of $H_2NN(R_1)C(O)R_2C(O)N(R_3)NH_2$ or of Formula I below

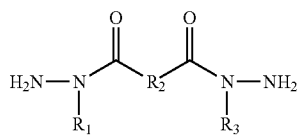

wherein $R_1$ and $R_3$ are independently selected from a C1 to C3 alkyl hydrocarbon, or an alkyl residue (such as a C1 to C3 alkyl residue for instance) bearing carboxylic, hydroxyl, sulfate, sulfonate, phosphate, alkyl ether, thiol, thiol ether, or amido functional groups and combinations thereof, wherein at least one of or, preferably, both of $R_1$ and $R_3$ is the C1 to C3 alkyl hydrocarbon or the alkyl residue, and $R_2$ is selected from a C1 to C12 alkyl hydrocarbon. In one approach, the modified dihydrazide compound is an alkyl modified hexanedihydrazide wherein the $R_1$ and $R_3$ groups are selected from the C1 to C3 alkyl hydrocarbon or the alkyl residue (such as a C1 to C3 alkyl reside bearing carboxylic, hydroxyl, sulfate, sulfonate, phosphate, alkyl ether, thiol, thiol ether, or amido functional groups and combinations thereof). In yet another approach, the modified dihydrazide is an alkyl modified hexanedihydrazide wherein the $R_1$ and $R_3$ groups are methyl. While the $R_1$ and $R_3$ alkyl hydrocarbons may, alternatively, be longer alkyl chains than three carbons to arrest the decomposition reactions herein, it is often preferred to maintain the chain length to 1 to 3 carbons to aid in maintaining the water solubility of the modified cross-linker. Thus, for applications that do not require water solubility of the cross-linker, the $R_1$ and $R_3$ chains may be longer than 3 carbons as needed for such applications.

Without wishing to be limited by theory, the presence of an alkyl group $R_1$ and $R_3$ (as those groups are discussed above) on the amide nitrogen of the hydrazide in Formulas I arrests or reduces the decomposition mechanism to nitrogen. Without wishing to be limited by theory, the amide nitrogen in the modified latent cross-linking compounds herein may arrest or reduce the decomposition mechanism because it does not bear a hydrogen that can be removed to make the nitrogen free to combine with the others to make a nitrogen molecule.

In some approaches, the polymer composition includes about 1 to about 10 weight percent of the modified latent cross-linking compound (based on the amounts of polymer and cross-linker only), in other approaches, about 2 to about 8 weight percent, and in yet other approaches, about 5 to about 7 weight percent, and in yet further approaches, about 2 to about 5 weight percent. Preferably, equimolar amounts of the dihydrazides herein and the carbonyl groups on the polymer are desired for cross-linking. In a paint system, the composition may include about 0.5 to about 8 weight percent of the modified cross-linking compounds herein, in other approaches, about 1 to about 8 weight percent, in other approaches, about 0.5 to about 5 weight percent, in other approaches, about 1.5 to about 3 weight percent, and in yet other approaches, about 1.5 to about 2.5 weight percent.

Latex Polymer

In one approach, the modified latent cross-linking compounds described herein are suitable for latex polymers or latex polymer systems that include one or more polymers having pendant ketone or carbonyl side groups thereon. For instance, the compositions may include one or more latex polymers or copolymers with acrylic, styrene acrylic, vinyl acetate, vinyl acrylic, or alkyd-acylic monomer units or blends thereof such as polymers or copolymers including ethylenically unsaturated monomers with at least carboxylic acid, alkyl acrylate, alkyl methacrylate, and/or acetate moieties. The polymers or copolymers may include as polymerizable or monomer units in a polymer backbone, one or more of vinyl monomers, acrylic monomers, and/or acrylate monomers such as vinyl acetate, alkyl acrylate, alkyl methacrylate, acrylic acid, styrene, and combinations thereof. Alkyl groups of such monomers may have chain lengths from 1 to 4 carbons and, in some approaches, are methyl, ethyl, propyl, isopropyl, n-butyl, t-butyl and the like side groups. The polymers or copolymers herein are also ketone or carbonyl-functional in that the polymers or copolymers also have additional monomer units including the functionality of a ketone, carbonyl, and/or aldehyde group that is a chain pendant and/or a terminal group on a polymer side chain.

In some approaches, the vinyl monomers or monomer units are selected from the group comprising or consisting of vinyl esters, vinyl aromatic hydrocarbons, vinyl aliphatic hydrocarbons, vinyl alkyl ethers and mixtures thereof. Examples of vinyl esters that may be used include vinyl acetate, vinyl propionate, vinyl laurate, vinyl pivalate, vinyl nonanoate, vinyl decanoate, vinyl neodecanoate, vinyl butyrates, vinyl benzoates, and vinyl isopropionate. Examples of vinyl aromatic hydrocarbons that may be used include styrene, methyl styrenes and other lower alkyl styrenes, chlorostyrene, vinyl toluene, vinyl naphthalene and divinyl benzene. Examples of vinyl aliphatic hydrocarbons that may be used include vinyl chloride and vinylidene chloride as well as alpha olefins such as ethylene, propylene, isobutylene, as well as conjugated dienes such as 1,3 butadiene, methyl-2-butadiene, 1,3-piperylene, 2,3-dimethyl butadiene, isoprene, cyclohexene, cyclopentadiene, and dicyclopentadiene. Examples of vinyl alkyl ethers that may be used include methyl vinyl ether, isopropyl vinyl ether, n-butyl vinyl ether, and isobutyl vinyl ether.

In other approaches, acrylic monomers or monomer units suitable for use in the polymers of the present disclosure include any compounds having acrylic functionality. Preferred acrylic monomers are selected from the group consisting of alkyl (meth)acrylates, acrylic acids, as well as aromatic derivatives of (meth)acrylic acid, acrylamides and acrylonitrile. Typically, the alkyl (meth)acrylate monomers (also referred to as alkyl esters of (meth)acrylic acid) can have an alkyl ester portion including from 1 to 12, and in some approaches, about 1 to 5, carbon atoms per monomer unit.

Suitable acrylic monomers or monomer units include, for example, methyl (meth)acrylate, ethyl (meth)acrylate, butyl (meth)acrylate, propyl (meth)acrylate, 2-ethyl hexyl (meth) acrylate, cyclohexyl (meth)acrylate, decyl (meth)acrylate, isodecyl (meth)acrylate, benzyl (meth)acrylate, isobornyl (meth)acrylate, neopentyl (meth)acrylate, 1-adamatyl methacrylate and various reaction products such as butyl, phenyl, and cresyl glycidyl ethers reacted with (meth)acrylic acid, hydroxyl alkyl (meth)acrylates, such as hydroxyethyl and hydroxypropyl (meth)acrylates, amino (meth)acrylates, as well as acrylic acids such as (meth)acrylic acid, ethacrylic acid, alpha-chloroacrylic acid, alpha-cycanoacrylic acid, crotonic acid, beta-acryloxy propionic acid, and beta-styryl acrylic acid.

(Meth)acrylate monomer(s) and monomer unit(s) include both acrylate monomer(s) and monomer unit(s) and methacrylate monomer(s) and monomer unit(s) as well as functionalized (meth)acrylate monomer(s) or monomer unit(s) suitable for incorporation into the polymers disclosed herein. Other examples of suitable (meth)aerylate monomers or monomer units include, but are not limited to, alkyl (meth)acrylates, including methacrylate, butyl acrylate, 2-ethylhexylacrylate, polyethyleneglycol acrylate or diacrylate, acetoacetoxyethyl acrylates, diacetone acyl halides, benxophenone (meth) acrylates, etc. Additionally, vinylic monomers or other monomers may be functionalized or include functional moieties that are utilized in post application functions, such as cross-linking, light or heat induced grafting. Functional moieties may also include crosslinking groups, photo-reactive groups, anti-fouling agents, light absorbers, anti-corrosion agents, and the like as needed for a particular application.

The polymer may also include monomers containing aromatic groups such as but not limited to styrene and/or methylstyrene. Suitable styrene monomers include, but are not limited to, styrene, methylstyrene, chlorostyrene, methoxystyrene and the like.

Pendant Ketone or Carbonyl-Functional Monomer:

The vinyl polymer or copolymers herein also includes monomer units polymerized therein including the pendant ketone or carbonyl-functional groups and may be formed by emulsion polymerization and/or free-radical addition polymerization of at least one ketone or carbonyl-containing monoethylenically unsaturated monomer with at least one other monomer unit discussed above that may not include the pendant ketone or carbonyl functionality. The monomer unit with the pendant ketone or carbonyl functional moiety may or may not have amido side group or a secondary nitrogen atom in the pendant chain with the ketone or carbonyl group. Examples of monoethylenically unsaturated monomers that include the pendant ketone or carbonyl-functional groups may include, but are not limited to, diacetone acrylamide, diaceatone methacrylamide, acrolein, methacrolein, crotonaldehyde, 4-vinylbenzaldehyde, vinyl alkyl ketones such as vinyl methyl ketone, and/or aceto acetoxy ethyl acrylate and combinations thereof.

The molecular weight of the vinyl polymers including the pendant ketone and/or carbonyl functional groups may have a number average molecular weight of about 15,000 to about 1,000,000; in other approaches, about 15,000 to about 500,000; in other approaches, about 15,000 to about 100, 000; in other approaches, about 15,000 to about 51,000; in other approaches, about 16,000 to about 28,000; and in yet other approaches, about 15,000 to about 16,000. In some approaches, the polymer compositions herein include about 90 to about 99 weight percent of the latex polymer (based on the total amounts of polymer and cross-linker only) in other approaches, about 94 to about 99 weight percent of the latex polymer, and in yet further approaches, about 96 to about 97 weight percent of the latex polymer. In a paint system, the composition may include about 10 to 60 weight percent polymer, in other approaches, about 20 to about 60 weight percent polymer, and in other approaches, about 40 to about 60 weight percent polymer, and in yet further approaches, about 40 to about 50 weight percent polymer.

Other Monomers or Polymers and Optional Components

The polymers or copolymers herein may include other optional monomer units polymerized into the polymer backbone or as additional, separate polymers as needed for a particular application. For instance, the backbone including the polymers or copolymers herein (or a separate polymer) may further include ureido monomers, amino monomers, sulfonate monomers or surfactants, silane monomers, phosphate monomers or surfactants, carboxyl monomers or surfactants, and combinations thereof. In some approaches, the polymers or copolymers may further include other vinyl monomers such as allyl imidazolidinone, allyl acetoacetates, allyl epoxies, epoxy acrylates, carbonyl monomers, other sulfonates, other phosphonates, vinyl phosphonate, allyl hydroxypropyl sodium sulfonate, allyloxy hydroxypropyl sodium sulfonate, and combinations thereof as needed for a particular application.

In some approaches, for instance, the other monomers in a polymer, copolymer, or terpolymer of the present disclosure, if included, may be in amounts up to about 10 weight percent, and in other approaches, about 0.1 to about 5 weight percent, in other approaches, about 0.5 to about 2 weight percent, but the amounts may vary depending on the particular application. In other approaches, the other or additional monomers may each be included in a polymer backbone in amounts less than about 1 weight percent.

In other approaches, a polymer may also include up to about 1 weight percent of ally imidazolidinone monomer to aid in the wet adhesion of the paint composition and up to about 1 weight percent of allyl hydroxypropyl sodium sulfonate monomer for stability to provide mechanical and thermal stability to the polymer and paint composition. In some approaches imidazolidone, sulfonate, and/or amide monomers are not needed.

The coating compositions herein may also include additional additives and components as needed for a particular application. For example and to suggest but a few additional components, the coating compositions may also include organic solvents, plasticizers, coalescing aids, pigments, extender pigment particles, colorants, dyes, emulsifiers, surfactants, preservatives, thickeners, heat stabilizers, leveling agents, anti-cratering agents, fillers, sedimentation inhibitors, ultraviolet-light absorbers, biocides, anti-foaming agents, freeze-thaw additives, Rheology modifiers, waxes, driers (i.e., drier salts), and the like and combinations thereof, to modify properties as needed for a particular application.

Pigment or Inorganic Particle

The coatings and coating compositions of the present disclosure may also include a pigment or inorganic particle. Suitable pigment particles or inorganic particles used in the compositions of the present disclosure may be titanium dioxide ($TiO_2$), zinc oxide ($ZnO_2$), calcium carbonate ($CaCO_3$) talc, clay materials, aluminum oxide, silicon dioxide, magnesium oxide, zinc sulfate, sodium oxide, potassium oxide, combinations thereof, or other known pigment or inorganic particles suitable for paints and other coatings. In some approaches, the pigment or inorganic particle is titanium dioxide, which may comprise anatase titanium dioxide or rutile titanium dioxide, or a mixture of the two. In other approaches, the pigment or inorganic particle comprises rutile titanium dioxide, to the exclusion of anatase titanium dioxide. In some approaches, the rutile titanium dioxide is surface treated with an inorganic oxide, such as silica ($SiO_2$). Generally, titanium dioxide has a particle size of from about 0.2 to about 0.3 microns in diameter and is provided in powder form, or in an aqueous slurry. An example of a titanium dioxide that is suitable for use in the present invention is Ti-Pure® R-706, which is commercially available from E.I. du Pont de Nemours and Company. Ti-Pure® R-706 titanium dioxide is a rutile titanium dioxide that is surface treated with silica.

In some approaches, the compositions may include about 0 to about 230 pounds of inorganic pigment (such as titanium dioxide) per 100 gallons of paint composition. In some approaches, the compositions herein may also include extender pigment particles (such a Omyacarb or Duramite, for example). If included, the extender pigment particles may be provided in about 24 to about 255 pounds per 100 gallons of paint composition Exemplary paint compositions including the polymers and modified cross-linking compounds are provided in Table 3 below

TABLE 3

| General Components of Compositions | | |
|---|---|---|
| Component | Broad Range, wt % | Narrow Range, wt % |
| Polymer with ketone | 10 to 60 | 15 to 25 |
| Cross-linker | 0.5 to 8 | 1.4 to 1.8 |
| Solvent | 30 to 70 | 45 to 65 |
| Pigment | 15 to 35 | 18 to 25 |

Preparation of Polymer Compositions and Latex Paring Compositions

The present disclosure also includes methods of making the polymer and coatings herein. If needed, the polymers can be synthesized through conventional emulsion polymerization techniques, and the paint composition can be prepared using standard mixing methods for paint and coatings manufacture. For instance, the coatings using the polymers of the present disclosure may be produced using conventional latex paint forming techniques including a grind and letdown process as known to those skilled in the art of manufacturing paint and coatings. In addition to the polymer component or binder latex described above (which may be the sole binder latex in the paints), an optional dispersant latex, an optional extender, and an optional thickener, the water-borne coating composition may contain conventional additives such as coalescing aids, biocides, anti-foaming agents, freeze-thaw additives, rheology modifiers, surfactants, preservatives, and the like and combinations thereof. It should also be appreciated that in addition to the pigment and the extender, small amounts of other pigments or colorants may be used to provide desired coloration or to confer other optical effects.

A proposed route of synthesis of the new alkyl modified cross-linking compound may include a multi-step process. First, adipic acid is reacted with a primary alkyl amine, such as a C1 to a C3 alkyl amine to form a dicarboxylic acid polyamine. Next, bromoacetate is combined with the dicarboxylic acid polyamine to form a bromo-modified dicarboxylic acid polyamine that can be reacted with ammonia to form the alkyl-modified dihydrazides of the present disclosure. An exemplary synthesis pathway is shown below.

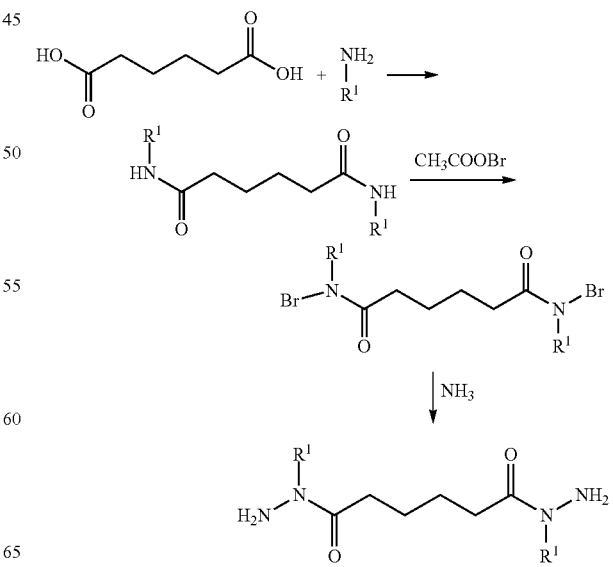

Another exemplary pathway to form the modified cross-linkers herein treats methylhydrazine with excess acetone and the mixture is then heated slowly while removing any distillate. Once cooled, trimethylamine is added followed by adipoyl chloride. The resulting mixture is hydrolyzed to the desired product. If needed, the reaction product may be purified by recrystallization. An exemplary pathway is shown by the reaction scheme below.

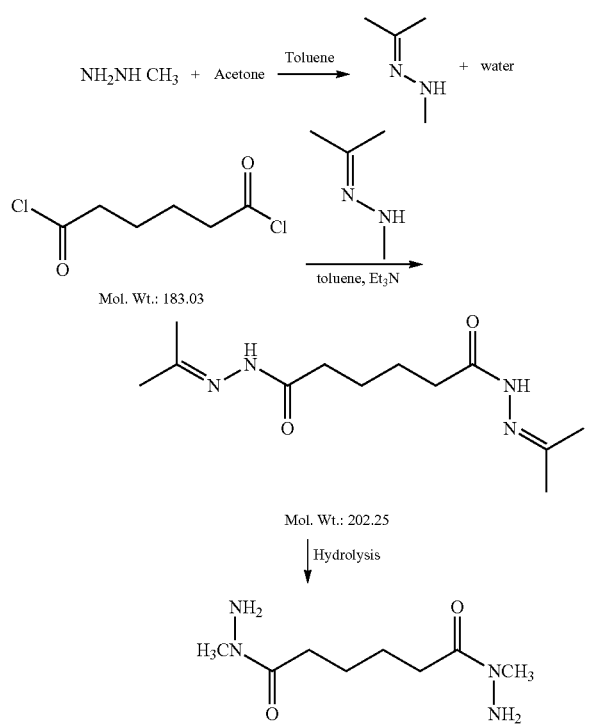

Glossary of Terms

Certain terminology is used herein for convenience only and is not to be taken as a limitation on the present invention. Relative language used herein is best understood with reference to the drawings (if any), in which like numerals are used to identify like or similar items. Further, in the drawings, certain features may be shown in somewhat schematic form.

It is also to be noted that the phrase "at least one of," if used herein, followed by a plurality of members herein means one of the members, or a combination of more than one of the members. For example, the phrase "at least one of a first component and a second component" means in the present application: the first component, the second component, or the first component and the second component combined. Likewise, "at least one of a first component, a second component, and a third component" means in the present application: the first component, the second component, the third component, the first component and the second component, the first component and the third component, the second component and the third component, or the first component and the second component and the third component. Similar combinations of larger listings of components are also possible.

"Scrubbability" or "Scrub" as used herein generally refers to the ability of the coating to resist erosion caused by scrubbing. Scrub is based on ASTM D2486-06 as described further in the Examples below.

"Washability" as used herein refers to the ability of a coating to exhibit stain resistance and stain removal properties. Washability is based on ASTM D3450-15 as described further in the Examples below.

"Adhesion" or "Wet Adhesion" as used herein refers to the ability of a dried coating to adhere to a glossy polyester paint (such as Sherwin Williams ProMar 200 Alkyd Semi-gloss) when wet. Adhesion is based on ASTM D6900-10 (reapproved 2015) as described further in the Examples below.

"Sheen" as used herein may also sometimes be referred to as "gloss". It is thought that because most extenders have a refractive index of light that is close to the refractive index of the binders of most coatings, below CPVC an extender/latex film will be largely transparent to visible light. In a coating, a gloss finish indicates that the surface which has a coating applied to it (i.e., is "finished") it is shiny or glass-like. The gloss of a surface is described as the reflection of light from the surface that is independent of color. ASTM D523 or D532-14 may be used to measure sheen. The prescribed angle at which light is reflected off the surface may vary, but for the purposes of this disclosure to measure 85 Sheen, is measured at 85° relative to the surface reflecting the light. ASTM D523 or D532-14 may also be used to describe 60 Gloss which is measured at 60° relative to the surface reflecting the light. One of skill in the art is able to determine relative levels of gloss (low versus high) in context of each coating.

"Pigment Volume Concentration" or "PVC" as used herein refers to a number that represents the volume of pigment (e.g., opaque polymer, titanium dioxide, and/or extender pigment particles) compared to the volume of all solids. In the field of paints and coatings, PVC is a useful measure because the Binder acts as the material to unite all the pigment and other raw materials into the paint and the PVC value ensures there is enough Binder to enable the paint to adhere properly to whatever it has been applied over in addition to containing all of the other components of the paint. If a paint has no pigment at all it will usually be very glossy and have a PVC of zero. An example is clear gloss paints. Flat paints have a very high pigment loading and have high PVCs (usually in the range from about 35% up to about 80%). Another non-limiting exemplary range of PVC in which pigment can be loaded is from about 60% to about 75%. Primers and undercoats vary from 30% to about 50% PVC as do semi-gloss, satin and low sheen paints. PVC may be expressed as a percentage. For example, if a coating has a PVC of 30, then 30% of the total binder and pigment blend is pigment and 70% of the total binder and pigment blend is binder solids on a volume basis.

"Binder" as used herein refers to long chain molecules of polymers or resins that are film-forming materials. Binders are generally responsible for gluing or binding coating materials together and to the substrate. Latex polymers are a non-limiting example of a Binder that may be dispersed in water using a dispersant and film formation (or other network formation) occurs by joining (or coalescence) of these solid particles as water evaporates or is otherwise driven off Exemplary Binders which may be used in the present disclosure include, but are not limited to, polyvinyl acetates, vinyl acrylics, styrene butadiene, styrene acrylics, ethylene vinyl polymers and copolymers or terpolymers as further discussed herein. In some approaches, the copolymers and terpolymers herein function as a paint binder and no further binder is utilized.

"Paint" as used herein refers to any mixture comprising different types of raw materials, each with its own function, which must be balanced to achieve the desired properties in the final product or film coating. The two primary functions of paint are decoration and protection. A paint may contain a solvent (which can include a volatile component derived from a petroleum distillate for a solvent-based paint, or a low VOC, or no-VOC, or water for a water-based paint), a Binder, a pigment, fillers (such as an extender or a plurality of extenders of different sizes) and an additive, which may impart different functionality to the paint or final coating. Embodiments may include a pigment cluster as a component thereof, optionally in combination with at least one of the solvent, Binder, pigment, filler and additive.

"Coatings" as used herein refer to compositions such as paint, stains, lacquers, etc.

"Additives" as used herein refer to a general category of components or other raw materials that may be added to the coatings herein to promote various properties. Examples include, but are not limited to, surfactants, defoamers, biocides, mildewcides, algaecides, thickeners, anti-settling agents, pH buffers, corrosion inhibitors, driers, and/or anti-skinning agents.

"Volatile Organic Compound" or "VOC" generally refers to organic compounds that have a high vapor pressure at room temperature. In many cases, VOC are compounds with a vapor pressure of greater than about 0.1 mm of Hg. VOC as reported herein is measured according to ASTM D2369-90 and is the weight of the VOC per volume of the coating solids in grams/L. As used herein, low VOC or substantially free of VOCs means less than about 5 g/L, in other approaches, less than about 1 g/L, and in yet other approaches, no VOC.

EXPERIMENTAL

The following examples demonstrate the preparation of polymers and paint compositions such as those described hereinabove. The examples are intended to be representative of the polymers and compositions that can be made and are not intended to limit the scope of the present disclosure to the specific illustrative examples disclosed below. All percentages, ratios, and amounts in these Examples and elsewhere in this disclosure are by weight unless otherwise specified.

Example 1

A one gallon can of a paint composition including a diacetone acrylamide containing acrylic or vinyl acrylic polymer having the prior un-modified adipic dihydrazide crosslinker was tested for outgassing. The paint composition included about 27 percent polymer, about 8 percent pigments, and the remaining was largely water and other conventional additives. This composition was evaluated after 180 days of shelf storage to determine the composition of the headspace gas using a gas chromatograph set-up to do light gas analysis. (Envantage, Inc, Cleveland, Ohio) This can of paint was experiencing visible can bulging after 180 days of storage.

The analysis of the gas is shown in the table 4 below, along with all the light gases the lab could detect. If no outgassing or oxygen depletion were occurring, the trapped air in the can should consist of about 78% nitrogen and about 21% oxygen and about 0.03% $CO_2$. However, the headspace gas in the bulging can including the unmodified ADH was clearly depleted in oxygen and enriched in nitrogen, which is believed to be the result of the outgassing due to the undesired reaction between the unmodified ADH (adipic dihydrazide) and possible metal contaminants in the system.

TABLE 4

| Headspace Light Gas analysis | |
|---|---|
| Compound | Mole % |
| Carbon Dioxide | 0.08 |
| Oxygen | 3.90 |
| Nitrogen | 96.02 |

Example 2

An experiment was conducted to measure gas production in latex solutions containing cross-linkers and doped with metal solutions to encourage gassing reactions. In this experiment, a modified version of adipic dihydrazide was compared to a standard adipic dihydrazide in an acrylic latex for the generation of nitrogen upon shelf storage.

Equipment used in this experiment including a 250 mL Erlenmeyer flask (threaded sidearm) with tubing connectors and O-ring compression seals, various sizes of tubing to connect the flask to a testing apparatus, zip ties and tubing clamps of appropriate sizes, a size 6 neoprene stopper, a VWR traceable logging manometer (−5 to +5 PSI range) or equivalent, and an environmental chamber set to 25 □C 50% RH to include the set-up for the experiment.

In this experiment, two 100 g test solutions (latex, cross-linker, and metal solutions) were prepared. For each experiment, each 100 gram acrylic latex solution (made with no cross-linker) was each placed into a separate flask, then either dry adipic dihydrazide (ADH-comparative) or an alkyl modified adipic dihydrazide consistent to the modified cross-linking compounds therein (Modified ADH-inventive compound with R1 and R3 being methyl and R2 being a C4 chain) was added and dissolved while stirring and adjusting the pH of the test solution to about 10 using trisodium phosphate. For the comparative ADH sample, 0.81% of test weight was needed to achieve the target pH, so about 0.81 g was added (FW 174.2 g/mol). For the inventive, modified-ADH sample, about 0.95% of test weight was needed to achieve the target pH, so about 0.94 g was added (FW 202.26 g/mol).

Each test solution contained about 120 ppm Cu and about 30 ppm Fe. This was accomplished by making 1% w/v solutions of Copper (II) Sulfate Pentahydrate (FW 249.68 g/mol) and Iron (III) Sulfate Hexahydrate (FW 399.88 g/mol). Once pH was stabilized, the metal solutions were added to each flask. For the 1% Cu (II) solution, about 4.7 mL was needed to achieve the target of about 120 ppm copper. For the 1% Fe (III) solution, about 2.1 mL was needed to achieve the target of about 30 ppm iron.

Each flask was then stirred vigorously to introduce air to mixture, then sealed with a stopper and attached to the manometer apparatus. The manometer was zeroed, and then set to record pressure continuously for 120 days. The pressure measurements were recorded every 12 hours. FIG. 1 shows the pressure of each flask over about 110 days. The data in FIG. 1 includes various peaks and valleys, which appeared be some type of systemic noise, maybe from the environmental chamber. Both manometers registered dip and spike measurements simultaneously.

As shown in FIG. 1, the comparative, prior ADH sample increased in pressure, which is believed to be due to nitrogen generation. The inventive, alkyl modified ADH (labeled as NG ADH in FIG. 1) had little to negligible pressure generation, which is believed due to the alkyl modified ADH arresting the nitrogen generation from the decomposition of the ADH. As understood herein, free of nitrogen gas means less than about 0.5 psi pressure increase due to nitrogen generation, in other approaches, less than about 0.25 psi pressure increase due to nitrogen generation, and in yet other approaches, no pressure increase due to nitrogen generation.

Example 3

An evaluation of the gel content of latex films was conducted, which indicates the extent of crosslinking. For this evaluation, neat films of latex, 10 mil, were cast on release paper and allowed to dry at ambient conditions for the pre-determined time as set forth in the table below. The dried films were then steeped in xylene for 24 hours. The swollen films were removed from the solvent, excess solvent was blotted off, and the weight was recorded. Then, the films were dried in oven at about 50° C. for about 16 hours and weighed again. Gel content was calculated as percent residual mass. Results are shown in Table 5 below.

TABLE 5

Gel Content

| Latex ID | Air-Dry Time/Days | Gel content |
| --- | --- | --- |
| NG-ADH Latex | 3 | 75% |
| NG-ADH Latex | 7 | 91% |
| ADH Latex | 3 | 88% |
| ADH Latex | 7 | 97% |

In Table 5, the Latex ID identified as "NG-ADH Latex" was a latex prepared with the inventive alkyl modified ADH as described herein and consistent with Example 2. The Latex ID identified as "ADH Latex" was a latex prepared with the prior unmodified ADH.

Example 4

An analysis was conducted to measure the scrub performance for latex paints using either the prior, unmodified ADH or the inventive alkyl modified ADH of the present disclosure and consistent with that in Example 2. In each evaluation, the latex paint formula was the same except for the ADH cross-linker. The results are presented in Table 6 below.

TABLE 6

| Latex ID | Gloss | Scrub (Paint) |
| --- | --- | --- |
| Latex with alkyl modified ADH | 20° 39 | 652 |
|  | 60° 80 |  |
| Latex with Prior ADH | 20° 46 | 750 |
|  | 60° 85 |  |

Unless otherwise specified, all measurements herein are made at 23±1° C. and 50% relative humidity. All publications, patent applications, and issued patents mentioned herein are hereby incorporated in their entirety by reference. Citation of any reference is not an admission regarding any determination as to its availability as prior art to the claimed invention.

The dimensions and values disclosed herein are not to be understood as being strictly limited to the exact numerical values recited. Instead, unless otherwise specified, such as dimension is intended to mean both the recited value and a functionally equivalent range surrounding that value. All ranges noted are intended to mean any endpoint within that range. For example, a dimension disclosed as "40 mm" is intended to mean "about 40 mm".

It is to be understood that each component, compound, substituent or parameter disclosed herein is to be interpreted as being disclosed for use alone or in combination with one or more of each and every other component, compound, substituent or parameter disclosed herein.

It is further understood that each range disclosed herein is to be interpreted as a disclosure of each specific value within the disclosed range that has the same number of significant digits. Thus, for example, a range from 1 to 4 is to be interpreted as an express disclosure of the values 1, 2, 3 and 4 as well as any range of such values.

It is further understood that each lower limit of each range disclosed herein is to be interpreted as disclosed in combination with each upper limit of each range and each specific value within each range disclosed herein for the same component, compounds, substituent or parameter. Thus, this disclosure to be interpreted as a disclosure of all ranges derived by combining each lower limit of each range with each upper limit of each range or with each specific value within each range, or by combining each upper limit of each range with each specific value within each range. That is, it is also further understood that any range between the endpoint values within the broad range is also discussed herein. Thus, a range from 1 to 4 also means a range from 1 to 3, 1 to 2, 2 to 4, 2 to 3, and so forth.

Illustrative embodiments have been described, hereinabove. It will be apparent to those skilled in the art that the above compositions and methods may incorporate changes and modifications without departing from the general scope of this disclosure. It is intended to include all such modifications and alterations within the scope of the present disclosure. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A dihydrazide cross-linking compound of the formula

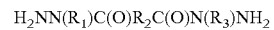

wherein $R_1$ and $R_3$ are independently selected from a C1 to C3 alkyl hydrocarbon or an alkyl residue bearing functional groups and $R_2$ is selected from a C1 to C12 alkyl hydrocarbon.

2. The dihydrazide cross-linking compound of claim 1, wherein the functional groups are selected from the groups consisting of carboxylic acid, hydroxyl, sulfate, sulfonate, phosphate, alkyl ether, thiol, thiol ether, amido groups and combinations thereof.

3. A coating composition to reduce nitrogen generation upon shelf storage, the coating composition comprising:
   a polymer with monomer units including a ketone or carbonyl thereon; and
   a cross-linking compound of the formula

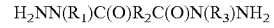

wherein $R_1$ and $R_3$ are independently selected from a C1 to C3 alkyl hydrocarbon or an alkyl residue bearing functional groups and $R_2$ is selected from a C1 to C12 alkyl hydrocarbon.

4. The coating composition of claim 3, wherein the functional groups are selected from the groups consisting of carboxylic acid, hydroxyl, sulfate, sulfonate, phosphate, alkyl ether, thiol, thiol ether, amido groups and combinations thereof.

5. The coating composition of claim 3, further comprising inorganic particles, but less than about 35 weight percent of the inorganic particles and one or more multivalent cation(s) is selected from the group consisting of copper, iron, manganese, tin, cobalt, chromium, vanadium, and mixtures thereof.

6. The coating composition of claim 3, wherein the polymer is selected from the group consisting of acrylic, acrylate, acetate, styrene, alkyd and combinations thereof monomer units.

7. The coating composition of claim 3, wherein the polymer is selected from the group is selected from the group consisting of polyacrylate, polyvinyl acetate-acrylate, polystyrene acrylate, or alkyd-acrylic hybrid polymers and wherein monomer units include a vinyl group polymerized into a polymer backbone and wherein at least one monomer unit has a side group extending from the vinyl group and having the ketone or carbonyl therein.

8. The coating composition of claim 3, wherein the polymer is an acrylic latex and the monomer units with the ketone or carbonyl thereon include a vinyl group polymerized into a polymer backbone and further includes a side group having an amido nitrogen and the ketone or carbonyl thereon.

9. The coating composition of claim 3, wherein the coating composition comprises about 45 to about 60 weight percent of the polymer and about 0.5 to about 5 weight percent of the cross-linking compound.

10. The coating composition of claim 5, wherein the coating composition comprises about 1 to about 500 ppm of the one or more multivalent cations(s).

11. The coating composition of claim 3, wherein the cross-linking compound comprises an alkyl modified hexanedihydrazide wherein the $R_1$ and $R_3$ group are methyl.

12. The coating composition of claim 3, wherein the monomer units with the ketone or carbonyl thereon are selected from the group consisting of diacetone acrylamide, diacetone methacrylamide, acetylacetoxy ethyl methacrylate, and combinations thereof.

13. The coating composition of claim 5, wherein the inorganic particles comprises titanium dioxide and wherein the coating composition includes about 1 to about 35 percent of the titanium dioxide.

14. A coating composition to reduce nitrogen generation, the coating composition comprising:
a polymer with monomer units including a ketone or carbonyl thereon;
a cross-linking compound of the formula $H_2NN(R_1)C(O)R_2C(O)N(R_3)NH_2$ wherein $R_1$ and $R_3$ are independently selected from a C1 to C3 alkyl hydrocarbon or an alkyl residue bearing functional groups and $R_2$ is selected from a C2 to C12 alkyl hydrocarbon;
inorganic particles, but less than about 35 percent of the inorganic particles; and
one or more multivalent cation(s) is selected from the group consisting of copper, iron, manganese, tin, cobalt, chromium, vanadium, and mixtures.

15. The coating composition of claim 14, wherein the functional groups are selected from the group consisting of carboxylic acid, hydroxyl, sulfate, sulfonate, phosphate, alkyl ether, thiol, thiol ether, amido groups and combinations thereof.

16. The coating composition of claim 14, wherein the monomer units with the ketone or carbonyl include an amido side group.

17. The coating composition of claim 14, wherein the polymer is an acrylic latex and the monomer units include a vinyl group polymerized into a polymer backbone and the monomer units having the ketone or carbonyl thereon include an amido side group with the ketone or carbonyl at a terminal end of the side group.

18. The coating composition of claim 14, wherein the coating composition comprises about 45 to about 60 weight percent of the polymer and about 0.5 to about 5 weight percent of the cross-linking compound.

19. The coating composition of claim 14, wherein the coating composition comprises about 1 to about 500 ppm of the one or more multivalent cations(s).

20. The coating composition of claim 14, wherein the cross-linking compound includes an alkyl modified hexanedihydrazide wherein the $R_1$ and $R_3$ groups are methyl.

21. The coating composition of claim 14, wherein the monomer units are selected from the group consisting of diacetone acrylamide, diacetone methacrylamide, acetylacetoxy ethyl methacrylate, and combinations thereof.

22. The coating composition of claim 14, wherein the inorganic particles comprise titanium dioxide and wherein the coating composition includes about 1 to about 35 percent of the titanium dioxide.

23. A cross-linked polymer comprising
a reaction product of (1) a polymer is selected from the group consisting of acrylic, acrylate, acetate, styrene, alkyd, urethane, or combinations thereof monomer units and monomer units with a pendant ketone or carbonyl thereon and (2) a cross-linking compound of the formula $H_2NN(R_1)COR_2CON(R_3)NH_2$ wherein $R_1$ and $R_3$ are independently selected from a C1 to C3 alkyl hydrocarbon or an alkyl residue bearing functional groups thereof and $R_2$ is selected from a C2 to C12 alkyl hydrocarbon; and
wherein the reaction of (1) and (2) occurs at about 20° C. to about 30° C. in the presence of one or more multivalent cation(s) is selected from the group consisting of copper, iron, manganese, tin, cobalt, chromium, vanadium, and mixtures thereof.

24. The cross-linked polymer of claim 23, wherein the functional group is selected from the group consisting of one of carboxylic, hydroxyl, sulfate, sulfonate, phosphate, alkyl ether, thiol, thiol ether, amido groups or combinations thereof.

25. The cross-linked polymer of claim 23, wherein prior to the formation of the reaction product of (1) and (2), a composition of an unreacted polymer (1) and an unreacted cross-linking compound (2) is free of nitrogen gas after 120 days of storage.

26. The cross-linked polymer of claim 23, wherein a dried coating composition including the cross-linked polymer exhibits at least 200 scrubs.

27. The cross-linked polymer of claim 23, wherein the polymer is an acrylic latex and includes a vinyl group polymerized into a polymer backbone and having an amido side group with the ketone or carbonyl therein.

28. The cross-linked polymer of claim 23, further comprising about 45 to about 60 percent of the polymer or copolymer and about 0.5 to about 5 percent of the cross-linking compound.

29. The cross-linked polymer of claim 23, wherein the reaction occurs in the presence of about 1 to about 500 ppm of the one or more multivalent cations(s).

30. The cross-linked polymer of claim 23, wherein the cross-linking compound includes an alkyl modified hexanedihydrazide wherein the $R_1$ and $R_3$ groups are methyl.

31. The cross-linked polymer of claim 23, wherein the monomer units are selected from the group consisting of diacetone acrylamide, diacetone methacrylamide, acetylacetoxy ethyl methacrylate, and combinations thereof.

32. The cross-linked polymer of claim 23, wherein the reaction product is included in a paint composition comprising about 1 to about 35 percent titanium dioxide.

\* \* \* \* \*